United States Patent [19]

Mimikos et al.

[11] Patent Number: 5,747,052
[45] Date of Patent: May 5, 1998

[54] AQUEOUS COMPOSITION TO NEUTRALIZE THE IRRITATING EFFECT OF CAPSAICIN ON EYES, SKIN AND MUCOUS MEMBRANES

[75] Inventors: Andrew N. Mimikos, Grosse Pointe Woods; Sam Rizzo, East Pointe, both of Mich.

[73] Assignee: Anthony Rizzo, East Pointe, Mich.

[21] Appl. No.: 488,901

[22] Filed: Jun. 9, 1995

[51] Int. Cl.⁶ ..................................... A61K 9/12
[52] U.S. Cl. .............. 424/402; 424/401; 424/47
[58] Field of Search .................. 424/401, 402, 424/45, 47

[56] References Cited

U.S. PATENT DOCUMENTS 4,443,362  4/1984  Guth et al. ..................... 252/545

OTHER PUBLICATIONS

Harry's Cosmeticology by Ralph Harry, pp. 65–67 (1973).

*Primary Examiner*—Jyothsna Venkat

[57] ABSTRACT

An aqueous composition to neutralize the irritating effect of capsaicin on the eyes, skin and mucous membranes, comprised of an neutralizing amount of a $C_xH_2{}_yO_y$ carbohydrate, where x and y are numbers and may be the same or different, a mild, nonirritating detergent to solubilize the capsaicin, an effective of amount of a pH adjustor to keep the pH in the range of from about 6.5 to 8, and the balance water.

12 Claims, No Drawings

AQUEOUS COMPOSITION TO NEUTRALIZE THE IRRITATING EFFECT OF CAPSAICIN ON EYES, SKIN AND MUCOUS MEMBRANES

BACKGROUND OF THE INVENTION

1. Field of the Invention.

The present invention relates to an aqueous composition to neutralize the irritating effect of capsaicin on the eyes, skin and mucous membranes, comprised of an effective amount of a $C_xH_{2y}O_y$ carbohydrate, where x and y are numbers and may be the same or different, a mild, nonirritating detergent, and effective of amount of a pH adjustor, and the balance water.

The present invention further relates to an aqueous compositions to neutralize the irritating effect of capsaicin on the eyes, skin and mucous membranes comprised of an effective amount of a mono, di or polysaccharide, or mixtures thereof, a mild, non irritating detergent, citric acid as a pH adjustor, and the balance water.

The present invention further relates to a tissue impregnated with an aqueous composition to neutralize the irritating effect of capsaicin on the eyes, skin and mucous membranes. The aqueous composition is comprised of an effective amount of a $C_xH_{2y}O_y$ carbohydrate, where x and y are numbers and may be the same or different, a mild, nonirritating detergent, and effective of amount of a pH adjustor, and the balance water.

The present invention further relates to a an aqueous spray to neutralize the irritating effect of capsaicin on the eyes, skin and mucous membranes. The aqueous spray composition is comprised of an effective amount of a $C_xH_{2y}O_y$ carbohydrate, where x and y are numbers and may be the same or different, a mild, nonirritating detergent, and effective of amount of a pH adjustor and the balance water.

2. Description of the Related Art.

Oleoresin Capsicum (OC) sprays have been known and used for a number of years as effective, non-lethal anti-personnel devices. The active ingredient is capsaicin, an alkaloid found in the Capsicum plant family.

The genus Capsicum has been used for centuries in the South American and Asian cuisines, and is what gives dishes of those cuisines their distinctive "hotness" or spiciness. Oleoresin Capsicum sprays are rated on the effectiveness of the capsaicin contained within them, as measured in Scoville Heat Units.

In 1912, a pharmacist named Wilbur Scoville developed the standard for measuring the perceived "hotness" of various peppers which are used in many pharmacological products. To determine the relative "hotness", Scoville ground pepper seeds into a mixture of alcohol, sugar and water, and submitted the mixture to a panel of five testers, who rated the "hotness" of the pepper based upon their collective subjective experience. Each pepper was rated upon the perceived "heat" perceived in the test, and rated according to units called Scoville Heat Units (SHU). The higher the SHU, the hotter the pepper. These subjective measurements have since been replaced with liquid chromatography.

There has been a long felt need to provide a field useable counter reactant to the Oleoresin Capsicum sprays currently in use. The present invention is directed to the field use of a counter reactant to Oleoresin Capsicum sprays.

SUMMARY OF THE INVENTION

The present invention is an aqueous composition to neutralize the irritating effect of capsaicin on the eyes, skin and mucous membranes, comprised of an effective amount of a $C_xH_{2y}O_y$ carbohydrate, where x and y are numbers and may be the same or different, a mild, nonirritating detergent, and effective of amount of a pH adjustor, and the balance water.

More particularly, the present invention further is an aqueous compositions to neutralize the irritating effect of capsaicin on the eyes, skin and mucous membranes comprised of an effective amount of a mono, di or polysaccharide, or mixtures thereof, a mild, non irritating detergent, citric acid as a pH adjustor, and the balance water.

More particularly, the present invention is an aqueous compositions to neutralize the irritating effect of capsaicin on the eyes, skin and mucous membranes comprised of from about 20 to 65 wt. percent, and more preferably about 20 to 40 wt. percent of a mono, di or polysaccharide, or mixtures thereof, from about 5 to 16 weight percent of a mild, non irritating detergent, from about 1 to 7 weight percent citric acid as a pH adjustor, and from about 50 to 70 weight percent water.

The present invention further relates to a tissue impregnated with an aqueous composition to neutralize the irritating effect of capsaicin on the eyes, skin and mucous membranes. The aqueous composition is comprised of an effective amount of a $C_xH_{2y}O_y$ carbohydrate, a mild, non-irritating detergent, an effective of amount of a pH adjustor, and the balance water.

The present invention further relates to an aqueous spray to neutralize the irritating effect of capsaicin on the eyes, skin and mucous membranes. The aqueous spray composition is comprised of an effective amount of a $C_xH_{2y}O_y$ carbohydrate, where x and y are numbers and may be the same or different, a mild, nonirritating detergent, and effective of amount of a pH adjustor, and the balance water.

Other objects will become apparent to those of ordinary skill in the art upon a reading of the appended specification and claims.

DETAILED DESCRIPTION OF THE PREFERRED EMBODIMENTS

The present invention is directed to an aqueous formulation for neutralizing the irritating effects of capsaicin to the eyes, skin and mucous membranes, as well and the means to dispense the aqueous formulation.

The preferred formulation is comprised of an effective amount of a $C_xH_{2y}O_y$ carbohydrate, where x and y are numbers and may be the same or different, a mild, nonirritating detergent, an effective of amount of a pH adjustor, and the balance water.

Of particular importance are the mono, di and poly saccharides. While any of the saccharides is expected to have some effect on reducing the perceived SHU of the capsaicin, those saccharides of particular use may be selected from the group consisting of glucose, fructose, maltose, lactose, mannose, sucrose and mixtures thereof. The mono, di or poly saccharides, or mixtures thereof are present in an amount of from about 20 to 65 wt. percent of the composition, and more preferably, from about 20 to 40 wt. percent of the composition.

In this regard, it has been surprisingly found that a mixture of 50 weight percent fructose and 50 weight percent sucrose has a synergistic effect on neutralizing the irritating effects of capsaicin, and as such, it is especially preferred to use such a mixture of fructose and sucrose as the saccharide component of the aqueous composition of the instant invention.

The detergent useful in the present invention is one which is mild and non irritating to the skin, eyes and mucous membranes. A preferred detergent composition is comprised of sorbitan PEG 80, cocamidopropyl betaine, sodium tridecth sulfate, sodium laurel amphoacetate, PEG 150 distearate, sodium laureth—13 carboxylate, citric acid, Quaternium 15, tetrasodium EDTA, propylene glycol methylparaben, propylparaben, imidazolididyl, urea and glycerin. Such a Detergent composition is called "Baby Shampoo" and is readily and commercially available from Johnson & Johnson of New Brunswick, New Jersey. The detergent is used to at least partially solubilize the capsaicin, and remove it from the skin. The detergent is present in an amount of about 5 to 16 weight percent of the composition.

An acid, such as citric acid, oxalic acid, acetic acid, hydrochloric acid, phosphoric acid, and mixtures thereof is used to control the pH so that the composition will not be too alkaline. It is preferred to keep the composition in the pH range of about 6.5 to about 8, and preferably in the range of from about a pH of 7 to 7.7. Generally, the acids are present in an amount of from about 0.1 to 1 percent by weight of the composition. The preferred acid is citric acid.

The balance of the composition is either deionized or tap water, and preferably deionized water. The water is present in an amount of from about 50 to 70 wt. percent of the composition.

The aqueous composition described above may be applied by a tissue impregnated with the aqueous composition to neutralize the irritating effect of capsaicin on the eyes, skin and mucous membranes.

The aqueous composition described above may also be applied by an aqueous spray to neutralize the irritating effect of capsaicin on the eyes, skin and mucous membranes.

The following examples are offered to illustrate various aspects of the invention. Those skilled in the art will appreciate that they are not to be construed as limiting in any way to the scope and spirit of the invention, as various modifications will occur to those of ordinary skill in the art.

In each of the following examples, a test subject is exposed, by direct contact in the face, to an Oleoresin Capsicum spray containing from about 1 to 10% capsaicin having an SHU rating of two millon, available from Fox Labs, Inc. of Clinton Township, Michigan, and the reaction of the test subject was recorded. Within 30 seconds, the test subjects reported tightness in the chest, difficulty in breathing, irritated mucous membranes, a severe burning sensation on the skin exposed to the spray, and the inability to open their eyes.

EXAMPLE 1

The test subject was exposed to the Oleoresin Capsicum spray, and the exposed area was flushed with large quantities of water. The test subject could not open his eyes and felt a burning sensation to the exposed skin, and experienced difficulty in breathing. It took 45 minutes of flushing with water before any noticeable relief was reported.

EXAMPLE 2

The test subject was exposed to the Oleoresin Capsicum spray and the exposed area was wiped by a tissue impregnated with a composition containing 40 wt. percent detergent, 12 wt. percent sucrose, 1 wt. percent citric acid, and the balance deionized water. The test subject reported that immediate relief of the burning sensation was felt, and he was able to re-open his eyes in about 8 minutes, and felt substantially recovered from the burning and irritating effects of the spray within 15 minutes.

We claim:

1. A tissue impregnated with an aqueous composition to neutralize the irritating effect of capsaicin on the eyes, skin and mucous membranes, comprised of a neutralizing amount of a $C_xH_{2y}O_y$ carbohydrate, where x and y are numbers and may be the same or different, and a mild, nonirritating detergent comprised of sorbitan PEG 80, cocamidopropyl betaine, sodium tridecth sulfate, sodium laurel amphoacetate, PEG 150 distearate, sodium laureth—13 carboxylate, citric acid, Quaternium 15, tetrasodium EDTA, propylene glycol methylparaben, propylparaben, imidazolididyl, urea and glycerin, said detergent present in an amount of from about 5 to 16 weight percent of the composition, an effective amount of a pH adjuster to keep the pH in the range of from about 6.5 to 8, and the balance water.

2. The equeous composition of claim 1, wherein the $C_xH_{2y}O_y$ carbohydrate, is selected from the group consisting of mono-, di-, and poly- saccharides, and mixtures thereof, present in an amount of from about 20 to 65 weight percent of the composition.

3. The aqueous composition of claim 1, wherein the pH adjustor is citric acid, oxalic acid, acetic acid, hydrochloric acid, phosphoric acid, or mixtures thereof, said pH adjustor present in an amount of from about 0.1 to 1 weight percent of the composition.

4. The aqueous composition of claim 1, wherein the water is present in an amount of from 50 to 70 weight percent of the composition.

5. The composition of claim 2, wherein the saccharides are sucrose and fructose, present in an amount of 50 weight percent fructose and 50 weight percent sucrose.

6. The composition of claim 1, wherein the pH is in the range of from about 7 to about 7.7.

7. A spray composition comprised of an aqueous composition to neutralize the irritating effect of capsaicin on the eyes, skin and mucous membranes, comprised of a neutralizing amount of a $C_xH_{2y}O_y$ carbohydrate, where x and y are numbers and may be the same or different, and a mild, nonirritating detergent comprised of sorbitan PEG 80, cocamidopropyl betaine, sodium tridecth sulfate, sodium laurel amphoacetate, PEG 150 distearate, sodium laureth—13 carboxylate, citric acid, Quaternium 15, tetrasodium EDTA, propylene glycol methylparaben, propylparaben, imidazolididyl, urea and glycerin, said detergent present in an amount of from about 5 to 16 weight percent of the composition, an effective amount of a pH adjuster to keep the pH in the range of from about 6.5 to 8, and the balance water.

8. The aqueous composition of claim 7, wherein the $C_xH_{2y}O_y$ carbohydrate is selected from the group consisting of mono-, di-, and poly- saccharides, and mixtures thereof, present in an amount of from about 20 to 65 weight percent of the composition.

9. The aqueous composition of claim 7, wherein the pH adjuster is citric acid, oxalic acid, acetic acid, hydrochloric acid, phosphoric acid, or mixtures thereof, said pH adjuster present in an amount of from about 0.1 to 1 weight percent of the composition.

10. The aqueous composition of claim 7, wherein the water is present in an amount of from 50 to 70 weight percent of the composition.

11. The composition of claim 8, wherein the saccharides are sucrose and fructose, present in an amount of 50 weight percent fructose and 50 weight percent sucrose.

12. The composition of claim 8, wherein the pH is in the range of from about 7 to about 7.7.

* * * * *